US00PP11338P

United States Patent [19]

Fruehwirth

[11] Patent Number: Plant 11,338

[45] Date of Patent: Apr. 11, 2000

[54] POINSETTIA PLANT NAMED 'ECKADONIS'

[75] Inventor: Franz Fruehwirth, Encinitas, Calif.

[73] Assignee: Paul Ecke Ranch, Inc., Encinitas, Calif.

[21] Appl. No.: 09/087,919

[22] Filed: Jun. 1, 1998

[51] Int. Cl.[7] ..... A01H 5/00

[52] U.S. Cl. ..... Plt./307

[58] Field of Search ..... Plt./307

[56] References Cited

U.S. PATENT DOCUMENTS

| | | | |
|---|---|---|---|
| P.P. 7,338 | 9/1990 | Hrebeniuk | Plt./307 |
| P.P. 7,825 | 3/1992 | Fruehwirth | Plt./307 |
| P.P. 7,883 | 6/1992 | Fruehwirth | Plt./307 |
| P.P. 10,162 | 12/1997 | Gross | Plt./307 |
| P.P. 10,763 | 1/1999 | Didden | Plt./307 |

OTHER PUBLICATIONS

GITM UPOVROM Citation for 'Ecke 34–97' as Per CA PBR 98–1449; Dec. 26, 1997.

*Primary Examiner*—Howard J. Locker
*Assistant Examiner*—Kent L. Bell
*Attorney, Agent, or Firm*—C. A. Whealy

[57] ABSTRACT

A new and distinct variety of Poinsettia plant named 'Eckadonis', characterized by its bright red flower bracts; dark green leaves; compact palnt habit; freely branching habit; and excellent postproduction longevity.

1 Drawing Sheet

BACKGROUND OF THE INVENTION

The present invention relates to a new and distinct variety of Poinsettia plant, botanically known as *Euphorbia pulcherrima* Willd., and hereinafter referred to by the name 'Eckadonis'.

The new variety is a naturally-occurring branch mutation of the commerical *Euphorbia pulcherrima* Willd. cultivar 'Red Sails', disclosed in U.S. Plant Pat. No. 6,980. The new Poinsettia was selected by the Inventor in a greenhouse in Encinitas, Calif., in 1996. The objective of the Inventor's Poinsettia development program is to create new Poinsettia cultivars having interesting bract and leaf display, desirable bract and foliage color and form, strong and freely branching stems and good post-production longevity.

Asexual reproduction of the new variety by terminal cuttings taken at Encinitas, Calif., has shown that the unique features of this new Popinsettia are stable and reproduced true to type in successive generations of asexual reproduction.

BRIEF SUMMARY OF THE INVENTION

The followiong traits have been repeatedly obsrerved and are determined to be the unique characteristics of 'Eckadonis'. These charaacteristics in combination distinguish 'Eckadonis' as a new distinct variety:

1. Bright red flower bracts.
2. Dark green leaves.
3. Compact plant habit.
4. Freely branching habit.
5. Excellent postproduction longevity.

In side-by-side comparisons conducted by the Inventor in Encinitas, Calif., plants of the new Poinsettia differed from plants of 'Red Sails' in the following characteristics:

1. Plants of the new Poinsettia are more compact, less vigorous and less open than plants of 'Red Sails'.

2. Flower bracts of plants of the new Poinsettia are brighter red in color than flower bracts of plants of 'Red Sails'.

4. Plants of the new Poinsettia flower later than plants of the cultivar 'Red Sails'.

BRIEF DESCRIPTION OF THE PHOTOGRAPH

The accompanying colored photograph illustrates the overall appearance of the new variety, showing the colors as true as it is reasonably possible to obtain a colored reproduction of this type. The photograph comprises a side perspective view of a typical plant of 'Eckadonis'.

DETAILED BOTANICAL DESCRIPTION

The new Poinsettia has not been observed under all possible environmental conditions. The phenotype may vary somewhat with variations in environment such as temperature, daylength and light intrensity, without, however, any variance in genotype. The following observations and measurements describe plants grown in Encinitas, Calif., under commercial practice in a polyethylene-covered greenhouse with day temperatures about 23° C, night temperatures about 17° C, and light levels about 40,000 lux. Plants were grown in 16.5—cm pots, pinched one time, and flowered under naturally lengthening nyctoperiods during the fall/early winter.

In the following description, color references are made to The Royal Horiotcultural Society Colour Chart except where general terms of ordinary dictionary significance are used.

Botanical clalssifications: *Euphorbia pulcherrima* Willd. 'Eckadonis'.

Parentage: Naturally-occuring branch mutation of *Euphorbia pulcherrima* Willd. cultivar *Red Sails*, disclosed in U.S. Plant Pat. No. 6,980.

Propagation:

*Type cutting.*—Terminal cuttings.

*Time to initiate roots.*—Summer: About 12 to 18 days at 27° C. Winter: About 15 to 18 days at 24° C.

*Time to develop roots.*—Summer: About 26 days at 27° C. Winter: About 26 days at 24° C.

*Rooting habit.*—Thick,freely brancing, becoming more fibrous with development.

Plant description:

*Plant form.*—Inverted triangle, rounded plant canopy.

*Growth habit.*—Compact, upright and slightly spreading. Freely branching, branching is enhanced by removing the shoot apex. Moderate growth rate and moderately vigorous.

*Plant height.*—About 28 cm.

*Crop time.*—From unrooted cuttings to a flowering plant in a 16.5—cm. container, about 18 weeks are required.

*Stem description.*—Appearance: Very thick, strong stems. Number of lateral branches: About six lateral branches are formed after removal of the terminal apex. Lateral branch length: About 23 cm. Internode length: About 7.5 mm. Stem color: 146A.

*Foliage description.*—Quantity of leaves per lateral branch: About 9. Length: About 12.5 cm. Width: About 8.5 cm. Shape: Mostly ovate with occasional irregular lobes. Apex: Acuminate. Base: Rounded to acute. Margin: Mostly entire, but occasionally irregular lobing. Texture: Smooth, dull, mostly glabrous with very slight pubescence on lower surface. Color: Young foliage, upper surface 147A. Young foliage, lower surface: 137B. Mature folioage, upper surface: Darker than 147A. Mature foliage, lower surface: 137A. Venation, upper surface: 147C. Venation, lower surface: 147D. Petiole: Length: About 7 cm. Diameter: About 3 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctopetriod conditions.

*Quantity of inflorescences.*—One per lateral branch, usually about six per plant.

*Inflorescence size.*—Diameter: About 30 cm. Height (depth): About 4.5 cm.

*Flower bracts.*—Quantity of flower bracts per inflorescence: Usually about 7 primary bracts and about 9 secondary bracts per inflorescence. Length: About 16.5 cm. Width: About 13.5 cm. Shape: Mostly ovate with occasional irregular lobes Apex: Abruptly acuminate. Base: Rounded to acute. Margin: Mostly entire, with ocasional irregular lobes Texture: Smooth, glabrous. Aspect: Mostly flat. Color: Developing, upper surface: More carmine than 45A. Developing, lower surface: 53C. Mature, upper surface: Brighter than 45A. Mature, lower surface: 45B.

*Cyathia.*—Quantity: Usually about 14 per corymb. Diameter of cyathia cluster: About 4.75 cm. Length: About 1.5 cm. Width: About 6 mm. Color: Immature: 144C. Mature: 144B/144C with red, 45A, ring at apex. Peduncle: Length: About 4 mm. Aspect: Strong, erect. Color: 144C. Stamens: Stamen number: Typicaly about 10 per cyathium. Anther size: About 1 mm. Anther shape: Oval Anther color: 9A. Amount of pollen: Moderate. Pollen color: 9A. Pistils: Pistil number: One per cyathium Stigma shape: Tri-lobate. Stigma color: 46A. Style length: About 1 mm. Style color: 46A. Nectary color: 23A.

Disease resistance: No fungal, bacterial nor viral problems observed on plants grown under commemrcial conditions.

Postproduction longevity: Generally plants maintain good substance and bract color for about four weeks under interior conditions.

It is claimed:

1. A new and distinct variety of poinsettia plant named 'Eckandonis', as illustrated and described.

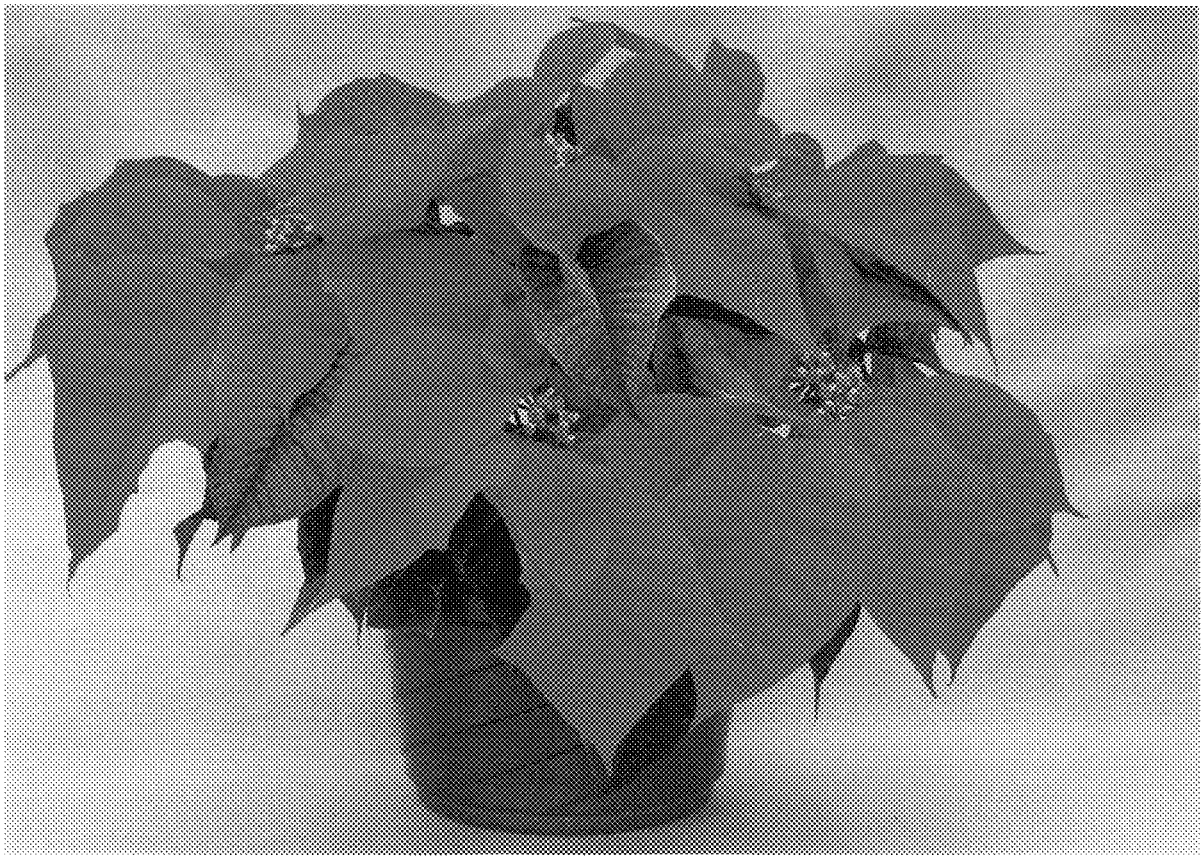

* * * * *